United States Patent [19]

Kohda et al.

[11] Patent Number: 5,217,897
[45] Date of Patent: Jun. 8, 1993

[54] PROCESS FOR CULTURING SAFFRON STIGMA TISSUES

[75] Inventors: Hiroshi Kohda; Kazuo Yamasaki, both of Hiroshima; Atsuko Koyama, Otake; Hideki Miyagawa; Naomi Fujioka, both of Hiroshima; Yuki Omori, Oita; Yoshiaki Ohta, Tokyo; Hiroshi Itoh, Ichikawa; Tsuyoshi Hosono, Chiba, all of Japan

[73] Assignee: Ohta's Isan Co., Ltd., Tokyo, Japan

[21] Appl. No.: 478,027

[22] Filed: Feb. 9, 1990

Related U.S. Application Data

[63] Continuation of Ser. No. 95,137, Sep. 11, 1987, abandoned.

[30] Foreign Application Priority Data

Sep. 20, 1986 [JP] Japan .................. 61-222500
May 30, 1987 [JP] Japan .................. 62-137440

[51] Int. Cl.$^5$ ............................................. C12N 5/04
[52] U.S. Cl. .......................... 435/240.45; 435/240.4; 435/240.46
[58] Field of Search .............. 435/240.45, 240.46, 435/240.97, 240.48, 240.49, 240.5, 240.51.240.54, 147.41

[56] References Cited

FOREIGN PATENT DOCUMENTS 52001   5/1982  European Pat. Off. .
0233040 8/1987  European Pat. Off. ....... 435/240.45

OTHER PUBLICATIONS

Product Information, SAN-EI Chemical Industries, Ltd.
Handbook of Oxalox Co., Ltd. for "Purelox", pp. 1-11, and chart.
Report of the Society for Antibacterial and Antifungal Agents, Japan, pp. 1-4.
Himeino et al. (1987) Agric. Biol. Chem 51(9): 2395-2400.
Sano et al. (1987) Plant Cell, Tissue and Organ Culture 11: 159-166.
Evans, et al. (1981) in TA Thorpe, ed. *Plant Tissue Culture*, Academic Press, NY, pp. 45-53.
Toshiake Matsuzaki et al., Plant Biotechnology, "Method of In-vitro Cultivation of Stigma Tissues" published by Kabushiki Kaisha Tokyo Kagaku Dojin, Apr. 25, 1986.
I. K. Vasil "Cell Culture and Somatic Cell Genetics of Plants", vol. 1, pp. 221–226, Academic Press Inc. (1984).
I. K. Vasil "Cell Culture and Somatic Cell Genetics of Plants", vol. 1, pp. 18–22, Academic Press Inc. (1984).

Primary Examiner—Che S. Chereskin
Attorney, Agent, or Firm—Spencer, Frank & Schneider

[57] ABSTRACT

This invention relates to a process for producing stigma-like tissues of saffron in a large scale by cutting the tissues of stigma (c), style (d, e, f), ovary (h, i, k), ovule (j), and petal (r) of saffron flower, and subculturing them on a liquid or solid LS medium or B5 medium containing a cytokinin and an auxin as main hormones.

12 Claims, 2 Drawing Sheets

PROCESS FOR CULTURING SAFFRON STIGMA TISSUES

This application is a continuation of application Ser. No. 07/095,137, filed Sep. 11, 1987 now abandoned.

FIELD OF THE INVENTION

This invention relates to a process for producing a substance having useful components of saffron such as crocein and the like on a large scale by tissue culture of the pistil of saffron (*Crocus sativus Linne*), which is an iridaceous plant.

The stigma moiety of saffron contains carotenoid pigments such as crocein and the like, picrocrocein which is a bitter glycoside, and saffronal which is an odoriferous element, and thus has been widely used for medicinal purposes and also as coloring agents and spices of food.

At present, the amount of its domestic consumption in Japan increases steadily each year, amounting to about 1 ton.

The dried pistils of saffron are extremely expensive, costing as much as 300 thousand yen to a million yen per kg.

CONVENTIONAL TECHNOLOGIES

As a process for producing a dried product of the stigmata of saffron, a method of cultivating saffron in a field, picking the stigmata at the time of flowering and drying them has conventionally been employed, but no producing method using a process of tissue culture of saffron stigma-like tissues has been known.

PROBLEMS TO BE SOLVED BY THE INVENTION

The conventional method of cultivating saffron in a field has the following disadvantages:
a. Saffron has a yield of only 3.6 kg–5.4 kg (as dried saffron) per acre even if the usual conditions are followed, so that the yield is low.
b. The flowering time is from October to November, during which the flowers must be picked. As the flowering time is as short as 15 days, however, unpicked flowers will remain if picking is not started simultaneously with the blooming.
c. The growth of saffron is influenced by the natural environment and weather may, so that an unseasonable weather unexpectedly result in an extreme reduction of the yield.
d. Saffron is mainly cultivated in European countries such as Spain and France and in Asia Minor, and is also cultivated in Japanese territory, especially in the Kyushu district and the Chugoku district.

As the repeated cultivation often causes blight, however, the cultivation can not be repeated for 5 years or more.

Thus, an increase in yield is hopeless in these circumstances.

In view of these disadvantages of the conventional cultivation method, the present invention provides a process for culturing stigma tissues of saffron which allows for its mass production at any time in any place without being influenced by the harvesting season.

Namely, this invention can achieve the present object by a process for culturing stigma tissues of saffron which comprises the following steps a–c:

a. a step of picking the portion of stigma, style, ovary, ovule, and petal of saffron and cutting it into each part,
b. a step of transplanting the cut tissues on a liquid or solid LS medium or B5 medium containing a cytokinin and an auxin, and
c. a step of subculturing the transplanted tissues under stationary, rotary or shaking culture.

Further, in order to achieve the more effective tissue culture, the following step is added:
d. a step of transplanting the tissues subcultured on the LS medium or B5 medium to a different medium successively, followed by subculturing.

As the cytokinin, kinetin (Ki), zeatin, or 6-benzyladenin (BA) is used.

As the auxin, indole-3-acetic acid (IAA), 1-naphthalenic acid (NAA) or indolebutyric acid (IBA) is used.

As hormones which can be used together, auxins such as 2,4-dichlorophenoxy acetic acid (2,4-D), 4-chlorophenoxy acetic acid (CPA) and the like and growth hormones such as gibberellic acid ($GA_3$), abscisic acid (ABA) and the like may be used.

The inorganic component in the medium include inorganic salts containing elements such as nitrogen, phosphorus, potassium, calcium, magnesium, sulfur, iron, manganese, zinc, boron, molybdenum, chlorine, iodine, cobalt and the like.

Examples of the carbon source in the medium include hydrocarbons such as sucrose and derivative thereof, organic acids such as fatty acid, and primary alcohols such as ethanol.

Vitamins in the medium include biotin, thiamine (vitamin $B_1$), pyridoxine (vitamin $B_6$), pyridoxol, pyridoxamine, calcium pantothenate, ascorbic acid (vitamin C), inositol, nicotinic acid, nicotinic amide, riboflavin (vitamin $B_2$) and the like.

As amino acids in the medium, for example, glycine, alanine, glutamic acid, cysteine, tyrosine, aspartic acid, amide arginine, and lysine may be used.

This invention is further illustrated in more detail according to the concrete embodiments.

EXAMPLE 1

Figure 1:
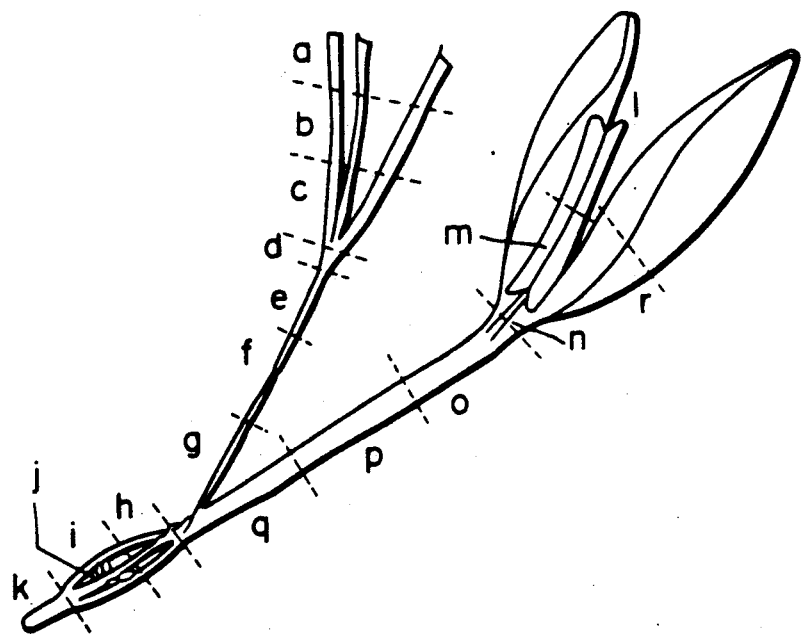
FIG. 1 shows a perspective view illustrating each moiety of the flower of saffron,
a ... Upper part of stigma
b ... Middle part of stigma
c ... Lower part of stigma
d ... Stigma style
e ... Upper part of style
f ... Middle part of style
g ... Lower part of style
h ... Upper part of ovary
i ... Lower part of ovary
j ... Ovule
k ... Part under ovule
l ... Upper part of anther
m ... Lower part of anther
n ... Filament
r ... Petal
o ... Upper part of the moiety continued from petal to ovary
p ... Middle part of the moiety continued from petal to ovary
q ... Lower part of the moiety continued from petal to ovary.
Figure 2:
FIG. 2 shows an enlarged photograph of the tissue q cultured in No. 25 of B5 medium (containing BA and NAA).
Figure 3:
FIG. 3 shows an enlarged photograph of the tissue q cultured in No. 25 of LS medium (containing BA and NAA).

Under the conditions as shown below, experiments over several generations were conducted, with respect to various concentration of each hormone and combination thereof, each medium and each culturing method, to find out the condition in which a tissue containing a yellow pigment can be cultured.

a. Preparation of section

A bud grown to about 6–13 cm from the bulb is cut off from the base and washed with flowing water.

The washed bulb is dipped in an Osvan-brand benzalkoniumchloride, by Takeda Chemical Industries, 100-fold solution for 5 minutes, in a Purelux-brand sodium hypochloride by Kabushiki Kaisha Ohyalux 10-fold solution for 5 minutes, and in 70% ethyl alcohol for 2–3 seconds, and then washed with a sterilized water three times. After washing, the bulb is taken out under aseptic conditions in a laboratory dish, and the stigma is cut off at the position slightly lower than the trilobate part, and the portion from the stigma to the ovary upper part is cut into 2 to 4 pieces so as to have a length of about 1–2.5 cm, for preparing planting sections.

b. Preparation of medium

As the basic medium, a liquid or 0.2% Gellan Gum-contained solid medium of Linsmaier Skoog medium (sucrose 30 g/l, pH 5.7–5.8) (hereinafter referred to as LS medium), Ganborg B5 medium (sucrose 20 g/l, pH 5.7–5.8) (hereinafter referred to as B5 medium), and White medium (sucrose 20 g/l, pH 5.7–5.8) were used.

The pH was adjusted using 0.1N KOH and 0.1N HCl after addition of the hormones.

c. Culturing method (1) Stationary culture

Stationary culture was carried out in a dark place with keeping the culturing room at 25°±3° C.

(2) Rotary culture

Rotary culture was carried out under the condition of 2 rpm (Kitagawa Tekkosho KW-1) in darkness with keeping the culturing room at 22°±1° C.

(3) Shaking culture

Shaking culture was carried out under the condition of 120 rpm (TAIYO ROTARY SHAKER R-11) in darkness with keeping the culturing room at 22°±1° C.

d. Hormones

The added hormones are selected from BA [6-benzyladenine, also referred to as BAP (6-benzylaminopurine)], zeatin, or kinetin (Ki) as the cytokinin and from IAA (indoleacetic acid), NAA (naphthaleneacetic acid), IBA (indolebutyric acid) or 2,4-D (2,4-dichlorophenoxyacetic acid) as the auxin.

The subculture was conducted by adding the combination of cytokinin and auxin as shown in Tables 1, 2, and 3 to each medium.

TABLE 1

| Auxin \ BA | B5 Medium | | | Unit: mol/l | |
|---|---|---|---|---|---|
| | 0 | $10^{-7}$ | $10^{-6}$ | $10^{-5}$ | $3 \times 10^{-5}$ |
| 0 | 1 | 6 | 11 | 16 | 21 |
| $10^{-7}$ | 2 | 7 | 12 | 17 | 22 |
| $10^{-6}$ | 3 | 8 | 13 | 18 | 23 |
| $10^{-5}$ | 4 | 9 | 14 | 19 | 24 |
| $5 \times 10^{-5}$ | 5 | 10 | 15 | 20 | 25 |

TABLE 2

| Auxin \ BA | LS Medium | | | Unit: mol/l | |
|---|---|---|---|---|---|
| | 0 | $10^{-7}$ | $10^{-6}$ | $10^{-5}$ | $3 \times 10^{-5}$ |
| 0 | 1' | 6' | 11' | 16' | 21' |
| $10^{-7}$ | 2' | 7' | 12' | 17' | 22' |
| $10^{-6}$ | 3' | 8' | 13' | 18' | 23' |
| $10^{-5}$ | 4' | 9' | 14' | 19' | 24' |
| $5 \times 10^{-5}$ | 5' | 10' | 15' | 20' | 25' |

TABLE 3

| Auxin \ BA | White Medium | | | Unit: mol/l | |
|---|---|---|---|---|---|
| | 0 | $10^{-7}$ | $10^{-6}$ | $10^{-5}$ | $3 \times 10^{-5}$ |
| 0 | 1" | 6" | 11" | 16" | 21" |
| $10^{-7}$ | 2" | 7" | 12" | 17" | 22" |
| $10^{-6}$ | 3" | 8" | 13" | 18" | 23" |
| $10^{-5}$ | 4" | 9" | 14" | 19" | 24" |
| $5 \times 10^{-5}$ | 5" | 10' | 15" | 20" | 25' |

(FIGS. in the tables indicate medium numbers)

The subculture was conducted every time by transplanting the tissues having r=5–10 mm (r represents a diameter of tissue) successively at intervals of 5–8 weeks.

e. Results

The state of the tissue or callus of the 4th generation was confirmed, and the results as shown in the following Tables 4–6 were obtained.

TABLE 4

| B5 Medium (Auxin: NAA) | |
|---|---|
| State of tissue or callus | Observed medium number |
| White to yellow callus was derived in 7 weeks | 15, 19, 20, 24, 25 |
| White to orange stigma-like tissues of 5–6 mm were differentiated in 3 months | 15, 19, 20, 24, 25 |
| Yellow to orange stigma-like tissues were differentiated in 4 months | 15, 19, 20, 24, 25 |

Particularly, in Nos. 24 and 25 mediums, a great number of stigma-like small process tissues were observed.

TABLE 5

| LS Medium (Auxin: NAA) | |
|---|---|
| State of tissue or callus | Observed medium number |
| White, transparent and soft callus was differentiated (partly hard) | 9', 10', 14', 15' 19', 20', 24', 25' |
| White stigma-like tissues were differentiated in 7 weeks to 3 months | 15', 19', 20', 24' 25' |
| A number of orange to yellow stigma-like tissues were differentiated in 3–4 months | 15', 19', 20', 24' 25' |

TABLE 6

| White Medium (Auxin: NAA) | |
|---|---|
| States of tissue or callus | Observed medium number |
| White to yellow callus was derived | 19", 20", 24" |

TABLE 6-continued

| White Medium (Auxin: NAA) | |
|---|---|
| States of tissue or callus | Observed medium number |
| in 7 weeks | |

The tissues in Nos. 15, 19, 20, 24, and 25 of B5 mediums in which a great number of stigma-like small process tissues were observed were transplanted to Nos. 7', 8', 9', 12', 13', and 14' of LS mediums, and the result shown in Table 7 was obtained.

Also, those in Nos. 15', 19', 20', 24', and 25' of LS mediums in which a great number of stigma-like small process tissues were observed were transplanted to Nos. 7, 8, 9, 12, 13, and 14 of B5 mediums, and the result shown in Table 8 was obtained.

TABLE 7

| Each No. of B5 medium → LS medium | |
|---|---|
| States of tissue or callus | Observed medium number |
| Changed to stigma-like tissues | All numbers |
| Trilobate tissues similar to the original plant were observed | 14' |

The tissues in Nos. 7'–9' have a tendency to become deeper red than those in Nos. 12'–14'.

TABLE 8

| Each No. of LS medium → B5 medium | |
|---|---|
| States of tissue or callus | Observed medium number |
| Changed to stigma-like tissues | All numbers |
| Trilobate tissues similar to the original plant were observed | 14 |

The tissues in Nos. 7–9 have a tendency to become deeper red than those in Nos. 12–14.

From the above results, it was proved that as the medium, LS mediums and B5 mediums are excellent for tissue culture (tissues having yellow pigments can be cultured) and derivation of callus, excepting a number of White mediums, As to the culturing method, all of stationary, rotary and shaking cultures were found to be suited for culture.

With respect to the combination in the medium numbers which afforded a satisfactory result among the LS mediums and B5 mediums containing NAA as the auxin and BA as the cytokinin, zeatin or kinetin was used instead of BA and almost the same result as the case of BA was obtained.

Also, when IBA, 2,4-D or IAA was used instead of NAA, mediums capable of culturing were hardly found for 2,4-D, and the tissue culture could be performed for IBA and IAA, although inferior compared with the case of NAA.

This shows that as the added hormones, BA is preferred as the cytokinin and NAA as the auxin.

Examination of the relation of the addition amounts of BA and NAA confirmed that Nos. 15, 19, 20, 24, and 25 of B5 medium in Table 1, Nos. 15', 19', 20', 24', and 25' of LS medium in Table 2, and Nos. 19'', 20'' and 24'' of White medium in Table 3 are excellent for tissue culture.

This shows that the hormone amounts of $10^{-6} - 3 \times 10^{-5}$ for BA and $10^{-5} - 5 \times 10^{-5}$ for NAA (unit is mol/l) suitable in B5 medium and LS medium, and the hormone amounts of $10^{-6} - 3 \times 10^{-5}$ for BA and $10^{-5} - 5 \times 10^{-5}$ for NAA (unit is mol/l) are suitable in White medium.

The subculture need not be conducted in the same medium, and the similar result can be obtained in transplanting tissues from B5 medium to LS medium or in the converse. In the case of successive transplantation, however, the culture is desirably conducted at a concentration lower than that of the previous medium.

Further, it was confirmed that those in which the tissues cultured in Nos. 15, 19, 20, 24 and 25 of B5 medium are transplanted to Nos. 7', 8', 9', 12', 13' and 14' of LS medium containing BA and NAA, those in which the tissues cultured in Nos. 15', 19', 20', 24', and 25' of LS medium are transplanted to Nos. 7, 8, 9, 12, 13, and 14 of LS medium containing BA and NAA, and those using LS medium and B5 medium containing BA of $10^{-7}$ and IAA of $10^{-7}$M are excellent for a high pigment-productive culturing.

As the B5 medium, Nos. 15, 19, 20, 24, and 25 containing BA and NAA proved to be excellent.

This shows that the hormone amounts in B5 medium and LS medium are suitably $10^{-7} - 10^{-6}$ for BA and $10^{-7} - 10^{-5}$ for NAA (mol/l) for high production of pigments.

As a result of TLC analysis and HPLC analysis, the cultured tissues proved to contain crocein and picrocrocein, similarly to the original plant.

EXAMPLE 2

Under the conditions as shown below, experiments over several generations were conducted, with respect to various concentration of each hormone and combination thereof, each medium and each culturing method, to find out the condition in which a tissue containing a yellow pigment can be cultured.

a. Preparation of section

A bud grown to about 6–13 cm from the bulb is cut from the base and washed with flowing water.

The washed bud is dipped in an osvan-brand benzalkonium chloride, of Takeda Chemical Industries 100-fold solution for 5 minutes, a Purelux-brand sodium hypochloride of Kabushiki Kaisha Ohyalux 10-fold solution for 5 minutes, and 70% ethyl alcohol for 2–3 seconds, and then washed with sterilized water three times. After washing, the bud is taken out under an aseptic condition in a laboratory dish and cut into the portions a–r as shown in the figure to prepare planting sections.

b. Preparation of medium

As the basic medium, fixed mediums in which 0.9% agar or 0.2% Gelrite-brand Gellan Gum of the Kelco Division of Merck & Co., Ltd. was added to Linsmaier Skoog (LS) medium (Sucrose 30 g/l, pH 5.7–5.8), Ganborg B5 medium (sucrose 20 g/l, pH 5.7–5.8) and White medium (sucrose 20 g/l, pH 5.7–8) were prepared.

The pH was adjusted using 0.1N KOH and 0.1N HCl after addition of the hormones.

c. Culturing method

Stationary, rotary, or shaking culture was carried out in a dark place with keeping the culturing room at 25°±3° C.

d. Plant hormone

As the plant hormones, a cytokinin and an auxin were added under various concentrations as shown in Table 9.

Each hormone used in the experiment is as follows:
Cytokinin: 6-benzyladenine (BA), kinetin (Ki), zeatin Auxin: indole-3-acetic acid (IAA), 2,4-dichlorophenoxyacetic acid (2,4-D), 1-naphthalenic acid (NAA), indolebutyric acid (IBA).

TABLE 9

| Auxin \ Cytokinin | 0 | $10^{-7}$ | $10^{-6}$ | $10^{-5}$ | $3 \times 10^{-5}$ |
|---|---|---|---|---|---|
| 0 | 1 | 6 | 11 | 16 | 21 |
| $10^{-7}$ | 2 | 7 | 12 | 17 | 22 |
| $10^{-6}$ | 3 | 8 | 13 | 18 | 23 |
| $10^{-5}$ | 4 | 9 | 14 | 19 | 24 |
| $5 \times 10^{-5}$ | 5 | 10 | 15 | 20 | 25 |

(FIGS. in the table indicate number of medium)

The subculture was conducted every time by transplanting the tissues having r=5–10 mm (r represents a diameter of tissue) successively at intervals of 5–8 weeks.

e. Results

As a result of examining the state of the tissues of the 4th generation, emergence of stigma-like tissues was observed in both B5 medium and LS medium, as shown in the following Tables 10–12.

TABLE 10

B5 Medium, LS Medium
Medium No. of BA-NAA combination

| Part | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|
| a | X | X | X | X | X | X | X | X | X | X | X | X | X | X | X |
| b | X | X | X | X | X | X | X | X | X | X | X | X | X | X | X |
| c | X | X | Δ | Δ | Δ | X | X | Δ | Δ | Δ | X | X | Δ | Δ | Δ |
| d | X | X | Δ | Δ | ○ | X | X | Δ | ○ | ○ | X | X | ○ | ○ | ○ |
| e | X | X | Δ | Δ | ○ | X | X | Δ | ○ | ○ | X | X | ○ | ○ | ○ |
| f | X | X | Δ | Δ | ○ | X | X | Δ | ○ | ○ | X | X | ○ | ○ | ○ |
| g | X | X | Δ | Δ | ○ | X | X | Δ | ○ | ○ | X | X | ○ | ○ | ○ |
| h | X | X | Δ | Δ | ⊙ | X | X | ○ | ○ | ⊙ | X | X | ○ | ⊙ | ⊙ |
| i | X | X | Δ | Δ | ○ | X | X | Δ | ○ | ○ | X | X | ○ | ○ | ○ |
| j | X | X | Δ | Δ | Δ | X | X | Δ | Δ | Δ | X | X | Δ | Δ | Δ |
| k | X | X | Δ | Δ | ○ | X | X | Δ | ○ | ○ | X | X | ○ | ○ | ○ |
| l | X | X | X | X | X | X | X | X | X | X | X | X | X | X | X |
| m | X | X | X | X | X | X | X | X | X | X | X | X | X | X | X |
| n | X | X | X | X | X | X | X | X | X | X | X | X | X | X | X |
| o | X | X | Δ | Δ | ○ | X | X | ○ | ○ | ⊙ | X | X | ○ | ⊙ | ⊙ |
| p | X | X | Δ | Δ | ○ | X | X | ○ | ⊙ | ⊙ | X | X | ○ | ⊙ | ⊙ |
| r | X | X | X | X | X | X | X | X | X | X | X | X | X | X | X |

⊙, ○, Δ, and X indicate the number of emergence of stigma-like tissues per piece after culturing for 4 months;
⊙ : 31 or more, ○ : 16–30, Δ: 5–15, X: hardly emerged.

TABLE 11

B5 Medium, LS Medium
Medium No. of BA-IAA combination

| Part | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|
| a | X | X | X | X | X | X | X | X | X | X | X | X | X | X | X |
| b | X | X | X | X | X | X | X | X | X | X | X | X | X | X | X |
| c | X | X | X | X | Δ | X | X | Δ | Δ | X | X | Δ | Δ | Δ | Δ |
| d | X | X | X | X | Δ | X | X | Δ | ○ | X | X | Δ | ○ | ○ | ○ |
| e | X | X | X | X | Δ | X | X | Δ | ○ | X | X | Δ | ○ | ○ | ○ |
| f | X | X | X | X | Δ | X | X | Δ | ○ | X | X | Δ | ○ | ○ | ○ |
| g | X | X | X | X | Δ | X | X | Δ | ○ | X | X | Δ | ○ | ○ | ○ |
| h | X | X | X | X | Δ | X | X | Δ | ○ | X | X | ○ | ○ | ○ | ○ |
| i | X | X | X | X | Δ | X | X | Δ | ○ | X | X | Δ | ○ | ○ | ○ |
| j | X | X | X | X | Δ | X | X | Δ | Δ | X | X | Δ | Δ | Δ | Δ |
| k | X | X | X | X | Δ | X | X | Δ | ○ | X | X | Δ | ○ | ○ | ○ |
| l | X | X | X | X | X | X | X | X | X | X | X | X | X | X | X |
| m | X | X | X | X | X | X | X | X | X | X | X | X | X | X | X |
| n | X | X | X | X | X | X | X | X | X | X | X | X | X | X | X |
| o | X | X | X | X | Δ | X | X | Δ | ○ | X | X | ○ | ○ | ○ | ○ |
| p | X | X | X | X | Δ | X | X | X | ○ | X | X | ○ | ○ | ○ | ○ |
| q | X | X | X | X | Δ | X | X | X | ○ | ○ | X | X | ○ | ○ | ○ |
| r | X | X | X | X | X | X | X | X | X | X | X | X | X | X | X |

⊙, ○, Δ, and X indicate the number of emergence of stigma-like tissues per piece after culturing for 4 months;
⊙ : 31 or more, ○ : 16–30, Δ: 5–15, X: hardly emerged.

TABLE 12

B5 Medium, LS Medium
Medium No. of BA-IBA combination

| Part | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|
| a | X | X | X | X | X | X | X | X | X | X | X | X | X | X | X |
| b | X | X | X | X | X | X | X | X | X | X | X | X | X | X | X |
| c | X | X | X | X | Δ | X | X | X | Δ | Δ | X | X | Δ | Δ | Δ |
| d | X | X | X | X | Δ | X | X | X | Δ | ○ | X | X | Δ | ○ | ○ |
| e | X | X | X | X | Δ | X | X | X | Δ | ○ | X | X | Δ | ○ | ○ |

TABLE 12-continued

| | B5 Medium, LS Medium | | | | | | | | | | | | | | |
|---|---|---|---|---|---|---|---|---|---|---|---|---|---|---|---|
| | Medium No. of BA-IBA combination | | | | | | | | | | | | | | |
| Part | 11 | 12 | 13 | 14 | 15 | 16 | 17 | 18 | 19 | 20 | 21 | 22 | 23 | 24 | 25 |
| f | X | X | X | X | Δ | X | X | X | Δ | ○ | X | X | Δ | ○ | ○ |
| g | X | X | X | X | Δ | X | X | X | Δ | ○ | X | X | Δ | ○ | ○ |
| h | X | X | X | X | Δ | X | X | X | Δ | ○ | X | X | ○ | ○ | ○ |
| i | X | X | X | X | Δ | X | X | X | Δ | ○ | X | X | Δ | ○ | ○ |
| j | X | X | X | X | Δ | X | X | X | Δ | Δ | X | X | Δ | Δ | Δ |
| k | X | X | X | X | Δ | X | X | X | Δ | ○ | X | X | Δ | ○ | ○ |
| l | X | X | X | X | X | X | X | X | X | X | X | X | X | X | X |
| m | X | X | X | X | X | X | X | X | X | X | X | X | X | X | X |
| n | X | X | X | X | X | X | X | X | X | X | X | X | X | X | X |
| o | X | X | X | X | Δ | X | X | X | Δ | ○ | X | X | ○ | ○ | ○ |
| p | X | X | X | X | Δ | X | X | X | ○ | ○ | X | X | ○ | ○ | ○ |
| q | X | X | X | X | Δ | X | X | X | ○ | ○ | X | X | ○ | ○ | ○ |
| r | X | X | X | X | X | X | X | X | X | X | X | X | X | X | X |

⊙, ○, Δ, and X indicate the number of emergence of stigma-like tissues per piece after culturing for 4 months;
⊙ : 31 or more, ○ : 16-30, Δ: 5-15, X: hardly emerged.

In Nos. 1-10 mediums having each combination of hormones, stigma-like tissues did not emerge.

The state of the tissues in No. 25 shown in Table 10 was grown as shown in Table 2 for B5 medium and in Table 3 for LS medium, after 3 months.

① In the mediums of White medium, no emergence was observed. This suggests that White medium is not suitable for culturing stigma-like tissues of saffron.

In comparison of B5 medium with LS medium, the number of emergence was higher in B5 medium by about 10%.

② The mediums having the combination of BA and 2,4-D showed no emergence in any medium number. This suggests that the auxin 2,4-D is not suitable for culturing stigma-like tissues.

Next, as a result of examining preferable auxins, NAA, IA and IBA were preferred in the order named.

③ The planting sections a, b, l, m, and n did not show the emergence of stigma-like tissues under any culturing conditions.

With respect to the emerging state of stigma-like tissues, it was found that q, p, o, h, d, e, g, f, and q are excellent in the order named, and q, p, and o are preferable.

④ Further, as to the mediums in which the results of mark ○ or ⊙ are obtained in each number of BA-NAA, BA-IAA, and BA-IBA, when Ki or zeatin was added instead of BA, almost the same result was obtained.

For the growing degree (the degree of growing the tissue), BA proved to be better than Ki by 5% or so. Accordingly, BA is preferable as the cytokinin.

However, there were hardly differences among the cytokinins. The reason can be considered that all the cytokinins belong to adenine.

⑤ When preferable concentrations of the cytokinin and the auxin were examined, it was found that, as a whole, the concentrations of $10^{-6}$-$3\times10^{-5}$ mol/l for the cytokinin and $10^{-6}$-$5\times10^{-5}$ mol/l for the auxin are preferable, although varied depending on planting sections.

⑥ Although agar and Gelrite-brand Gellan Gum of the Kelco Division of Merck & Co., Ltd. were used to make a solid medium, the growing degree is 5-10% higher in those containing 0.2% Gelrite-brand Gellan Gum than those containing 0.9% agar.

In this example, the mediums having the combinations indicated in Nos. 1-12 did not show the emergence of stigma tissues, but when the tissues emerged in Nos. 24 or 25 were transplanted successively to Nos. 7, 8, 9, 10, 12, 13, 14, or 15 similarly to the first example described above, the stigma tissues were cultured to produce the pigments more highly.

This revealed that the culture is preferably conducted at low concentrations of the hormones, after the tissues have been once emerged.

This effect was further increased by adding $10^{-6}$-$10^{-5}$ M of gibberellic acid (GA$_3$).

Effects

As illustrated so far, according to the process for tissue culture of this invention, saffron stigma tissues can be produced in a large scale and in a short time without limiting the harvesting season and the districts, compared with the conventional cultivation process of saffron.

What is claimed is:

1. A process for producing saffron stigma tissues which comprises the following steps:
   a. selecting at least one portion of saffron selected from the group consisting of stigma, style, ovary, and ovule, and cutting the selected portion into pieces,
   b. transplanting the cut tissues on a liquid or solid LS medium or B5 medium containing at least one cytokinin selected from benzylaminopurine, kinetin, and zeatin and at least one auxin selected from NAA, IBA, and IAA as main hormones, and
   c. subculturing the transplanted tissues under stationary, rotary or shaking culture to produce saffron stigma tissues.

2. A process for producing saffron stigma tissues according to claim 1 in which gibberellic acid (GA$_3$) is added as a hormone.

3. A process for producing saffron stigma tissues according to claim 1 in which the concentration of the cytokinin is from about $10^{-6}$ to $3\times10^{-5}$ mol/l.

4. A process for producing saffron stigma tissues according to claim 1 in which the auxin is NAA.

5. A process for producing saffron stigma tissues which comprises the following steps in the following order:
   a. a step of selecting at least one portion of saffron selected from the group consisting of stigma, style, ovary, and ovule, and cutting the selected portion into pieces, b. a step of transplanting the cut tissues on a liquid or solid LS medium or B5 medium containing at least one cytokinin in a concentration from about $10^{-6}$ to $3 \times 10^{-5}$ mol/l selected from benzylaminopurine, kinetin, and zeatin and at least one auxin in a concentration from about $10^{-6}$ to $5 \times 10^{-5}$ mol/l selected from NAA, IBA, and IAA as main hormones, c. a step of subculturing the transplanted tissues under stationary, rotary, or shaking culture, and d. a step of transplanting the tissues cultured on the LS medium or B5 medium in step c to a different medium containing a lower concentration of cytokinin or auxin than the medium in step b, followed by subculturing to produce saffron stigma tissues.

6. A process for producing saffron stigma tissues according to claim 5 in which gibberellic acid ($GA_3$) is added as a hormone.

7. A process for producing saffron stigma tissues according to claim 2 in which the concentration of the cytokinin is from about $10^{-6}$ to $3 \times 10^{-5}$ mol/l and the concentration of the auxin is from about $10^{-6}$ to $5 \times 10^{-5}$.

8. A process for producing saffron stigma tissues according to claim 3 in which the auxin is NAA.

9. A process for producing saffron stigma tissues according to claim 2 in which the auxin is NAA.

10. A process for producing saffron stigma tissues which comprises the following steps:

a. selecting at least one portion of saffron selected from the group consisting of stigma, style, ovary, and ovule, and cutting the selected portion into pieces, b. transplanting the cut tissues on a liquid or solid LS medium or B5 medium containing at least one cytokinin in a concentration from about $10^{-6}$ to $3 \times 10^{-5}$ mol/l selected from benzylaminopurine, kinetin, and zeatin and at least one auxin in a concentration from about $10^{-6}$ to $5 \times 10^{-5}$ mol/l selected from NAA, IBA and IAA as main hormones, and c. subculturing the transplanted tissues under stationary, rotary or shaking culture to produce saffron stigma tissues.

11. A process for producing safforon stigma tissues according to claim 10 in which gibberellic acid ($GA_3$) is added as a hormone.

12. A process for producing saffron stigma tissues according to claim 5 in which the concentration of the cytokinin in the medium to which the tissues are transplanted in step d from about $10^{-7}$ to $10^{-6}$ mol/l and concentration of the auxin is from about $10^{-7}$ to $10^{-5}$ mol/l.

* * * * *